(12) United States Patent
He et al.

(10) Patent No.: US 11,753,672 B2
(45) Date of Patent: Sep. 12, 2023

(54) SWAB SAMPLE NUCLEIC ACID RELEASER AND USE THEREOF

(71) Applicant: DA AN GENE CO., LTD., Guangdong (CN)

(72) Inventors: Yunshao He, Guangdong (CN); Xiwen Jiang, Guangdong (CN); Qiao Xia, Guangdong (CN); Zhiqiang Dong, Guangdong (CN); Lili Liao, Guangdong (CN); Hanrong Li, Guangdong (CN)

(73) Assignee: DA AN GENE CO., LTD., Guangdong (CN)

( * ) Notice: Subject to any disclaimer, the term of this patent is extended or adjusted under 35 U.S.C. 154(b) by 81 days.

(21) Appl. No.: 17/284,476

(22) PCT Filed: Oct. 27, 2020

(86) PCT No.: PCT/CN2020/124134
§ 371 (c)(1),
(2) Date: Apr. 12, 2021

(87) PCT Pub. No.: WO2021/248779
PCT Pub. Date: Dec. 16, 2021

(65) Prior Publication Data
US 2022/0145356 A1    May 12, 2022

(30) Foreign Application Priority Data

Jun. 12, 2020  (CN) .......................... 202010538226.2

(51) Int. Cl.
*C12Q 1/6806* (2018.01)

(52) U.S. Cl.
CPC .................. *C12Q 1/6806* (2013.01)

(58) Field of Classification Search
CPC .......................... C12Q 1/6806; C12N 15/1003
See application file for complete search history.

(56) References Cited

U.S. PATENT DOCUMENTS

| 2004/0043505 A1* | 3/2004 | Walenciak | A61B 5/150755 |
| | | | 422/400 |
| 2005/0009036 A1 | 1/2005 | Montesclaros et al. | |
| 2006/0153870 A1* | 7/2006 | Parks | A61K 39/00 |
| | | | 435/235.1 |
| 2012/0052572 A1* | 3/2012 | Whitney | A01N 1/021 |
| | | | 252/400.1 |
| 2016/0108463 A1* | 4/2016 | Fischer | C12Q 1/6876 |
| | | | 435/6.12 |
| 2016/0333339 A1 | 11/2016 | Fischer et al. | |

FOREIGN PATENT DOCUMENTS

| CN | 1891833 | 1/2007 |
| CN | 105143449 | 12/2015 |
| CN | 105463125 | 4/2016 |
| CN | 106574265 | 4/2017 |
| CN | 106591488 | 4/2017 |
| CN | 106995842 | 8/2017 |
| CN | 107227306 | 10/2017 |
| CN | 107227345 | 10/2017 |
| CN | 109402239 | 3/2019 |
| CN | 109486903 | 3/2019 |
| CN | 109694901 | 4/2019 |
| CN | 111172239 | 5/2020 |
| EP | 1354036 | 10/2003 |

OTHER PUBLICATIONS

Wikipedia Entry for Gunidine thiocyanate (Year: 2022).*
"International Search Report (Form PCT/ISA/210) of PCT/CN2020/124134," dated Mar. 17, 2021, pp. 1-7.
Tang Shuming et al., "Principle of isolation and purification of nucleic acid and its methodologic progress", Sect Clin Biochem & Lab Med Foreign Med Sci, vol. 26 ,No. 3, Mar. 31, 2005, pp. 1-4.
Zhong Huiyu et al., "Clinical points and experience in nucleic acid testing of SARS-CoV-2", Int •523• J Lab Med, Mar. 2020,vol. 41,No. 5, Mar. 31, 2020, pp. 1-5.
Kuang Hui-Hu et al., "Detection of nucleic acid of 2019-nCoV in medical laboratory and its practice", Chin J Nosocomiol vol. 30 No.6 2020, Mar. 31, 2020, pp. 1-5.

* cited by examiner

*Primary Examiner* — Ethan C Whisenant
(74) *Attorney, Agent, or Firm* — JCIP GLOBAL INC.

(57) ABSTRACT

The present invention discloses a swab sample nucleic acid releaser and use thereof. The sample releaser includes 1-20 mol/L of a metal ion chelating agent, 5-80 mmol/L of a buffer at pH 6-9, 5%-40% (v/v) of a polar organic solvent, 0.2%-10% (v/v) of a surfactant, and 0.1-1 mol/L of a nuclease inhibitor. The sample releaser can integrate three steps of sampling and preservation, inactivation, and nucleic acid extraction into one step, and after sampling, the sample can be directly put into a sampling tube equipped with the sample releaser for storage and transportation; and when in use, the sampling tube is turned upside down and mixed well, and after the sample and the sample releaser are fully mixed, it is let stand for a few minutes at room temperature to release the nucleic acid of the sample.

3 Claims, 1 Drawing Sheet

SWAB SAMPLE NUCLEIC ACID RELEASER AND USE THEREOF

CROSS-REFERENCE TO RELATED APPLICATION

This application is a 371 of international application of PCT application serial no. PCT/CN2020/124134, filed on Oct. 27, 2020, which claims the priority benefit of China application no. 202010538226.2, filed on Jun. 12, 2020. The entirety of each of the above mentioned patent applications is hereby incorporated by reference herein and made a part of this specification.

TECHNICAL FIELD

The present invention belongs to the technical field of pathogen molecular detection, and more specifically, relates to a swab sample nucleic acid releaser with simple operation and quick release and use thereof.

BACKGROUND

Molecular test of nucleic acid has incomparable advantages in the detection and screening of pathogens and has a wide range of applications. For example, in the recent outbreak of 2019-nCoV epidemic, nucleic acid testing has played a key role in the screening and testing of infected and asymptomatic people, and is of great significance to epidemic control. At present, swab sample is mainly used in the detection of pathogens such as viruses and genetic disease screening, including nasal swabs, throat swabs, oral swabs, anal swabs, etc. Because of its convenient collection, transportation and storage, it is widely used. However, the amount of cells collected using swabs is very limited, and the conditions for cell growth and storage are extremely stringent. After transportation and storage at room temperature, it causes a lot of damage to the cells in the swab, which makes it easy to cause false positives or false negatives in downstream experiments.

At the same time, extraction of nucleic acid is an indispensable part of the detection of nucleic acid. The extraction and purification of nucleic acid generally go through the steps of lysis-washing-elution of the sample. At present, the main nucleic acid extraction reagents on the market include column extraction method and paramagnetic particle method. Nucleic acid extracted by the column extraction method and paramagnetic particle method has the advantage of high purity, but at the same time there are the disadvantages of cumbersome operation and the need to use corresponding extraction equipment, which leads to higher costs. It is very unsuitable for swap samples that have a relatively small sample size and are difficult to store and transport. At present, the storage of swab samples in the market is basically based on physiological saline or sample preservation solution, and a certain amount of sample needs to be taken for nucleic acid extraction during use. The collected swab samples generally require high temperature inactivation. When high temperature inactivation is performed, more aerosol pollution is likely to occur, which makes laboratories and experimental operators have a higher risk of contamination.

Patent application No. 201811598212.9 provides an elution lysate for eluting and lysing the cells on the swab to release nucleic acid, but the method of using the lysate still requires high temperature processing of the sample, and two steps are required: first immersing the swab sample in the elution lysate, vortex blending, and incubating at 37° C. for 60 minutes; then opening the lid again to take out the swab, and then placing the centrifuge tube after taking out the swab in a water bath at 65° C. for 5 minutes, and a water bath at 95° C. for 10 minutes, and taking a supernatant as a solution to be detected. It can be seen that the method is not as simple as it claims, and it is time-consuming, and high temperature processing is easy to damage the nucleic acid to a certain extent, lose the amount of nucleic acid, and easily cause the aerosol pollution problem mentioned above.

In short, the current nucleic acid extraction from swab samples has at least the following disadvantages: (1) high temperature inactivation of samples is required, which causes a risk of contamination to operators and laboratories, and will lose the amount of nucleic acid; (2) it is necessary to perform additional extraction of nucleic acid from the samples, which makes the operation process more complicated and clinically increases time from collection of samples to results; and (3) there are certain professional skills requirements for the test personnel, and the quality of the test results is closely related to the operation process of the test personnel.

SUMMARY

The technical problem to be solved by the present invention is to overcome the shortcomings and deficiencies of the above-mentioned prior art, and to provide a simple, efficient, and rapid swab sample nucleic acid extraction reagent and an extraction method, which is a direct lysis method to release nucleic acid in the sample. Under the action of the sample releaser of the present invention, a cell membrane is quickly destroyed, so that the nucleic acid is released, and the released nucleic acid can be added to a PCR system for amplification and detection. The sample releaser of the present invention can be used to extract the nucleic acid of a nasopharyngeal swab sample, and a whole process is extremely simple and fast and there is no need for any lid-opening operation midway, and no high temperature treatment. It can release and obtain the nucleic acid in the sample most efficiently, without affecting the subsequent PCR amplification, and without any risk of contamination and infection.

An objective of the present invention is to provide a swab sample nucleic acid releaser.

Another objective of the present invention is to provide use of the swab sample nucleic acid releaser.

The above-mentioned objectives of the present invention are achieved by the following technical solution.

A swab sample nucleic acid releaser includes the following components:
(1) 1-20 mol/L of a metal ion chelating agent;
(2) 5-80 mmol/L of a buffer at pH 6-9;
(3) 5%-40% (v/v) of a polar organic solvent;
(4) 0.2%-10% (v/v) of a surfactant; and
(5) 0.1-1 mol/L of a nuclease inhibitor.

In particular, preferably, the metal ion chelating agent includes but is not limit to one or more of EDTA, EGTA and citric acid.

Preferably, the buffer includes but is not limit to Trisbuffer, sodium citrate buffer, sodium phosphate buffer or sodium acetate buffer.

Preferably, the polar organic solvent includes but is not limit to one or more of DMSO, hexamethylphosphoramide, and N,N,N',N'-Tetramethylethylenediamine.

Preferably, the surfactant includes but is not limit to one or more of Triton X-100 t-octylphenoxypolyethoxyethanol), Nonidet P-40 (nonylphenoxypolyethoxyethanol), Tween-20 (polysorbate 20) and SDS.

Preferably, the nuclease inhibitor includes but is not limit to guanidine hydrochloride, guanidine isothiocyanate or 4,4'-carbonylbis(2-(1-naphthoylamino)benzoic acid).

Preferably, the metal ion chelating agent has a concentration of 5 mol/L, and the buffer has a concentration of 50 mmol/L and pH 8.5.

Preferably, the polar organic solvent has a concentration of 25%.

Preferably, the surfactant has a concentration of 2%.

Preferably, the nuclease inhibitor has a concentration of 0.3 mol/L.

A use method of the sample releaser in the present invention is as follows: putting a swab into a container containing the sample releaser, turning the container upside down for 5-10 times or mixing for 20-40 seconds at room temperature, letting stand for 5-20 minutes (preferably 5-10 minutes), and turning upside down again for 5-10 times or mixing for 20-40 seconds, after an instantaneous centrifugation, a supernatant is the released nucleic acid solution, and the resulting nucleic acid solution can be used for PCR amplification. The swab sample is stored, transported, and verified and released in the sample releaser. There is no need to open the lid during the whole process. It is safe and efficient, and the operation is extremely simple, and the application is very wide.

Thus, use of the sample releaser in preparing a swab sample nucleic acid releasing kit, and the developed swab sample nucleic acid releasing kit containing the sample releaser, should be within the scope of protection of the present invention.

The present invention has the following beneficial effects.

The sample releaser developed in the present invention can integrate three steps of sampling preservation-inactivation-nucleic acid extraction into one step. After sampling, it can be directly put into the sampling tube equipped with the sample releaser for storage and transportation; and when in use, the sampling tube is turned upside down and mixed well, and after the sample and the sample releaser are fully mixed, it is let stand for 15 minutes at room temperature to inactivate the sample and at the same time release the nucleic acid of the sample. The entire operation process does not require heating and lid opening midway, which effectively avoids the contamination of experimental operators and laboratories, and simplifies the operation of nucleic acid extraction to the greatest extent.

The sample releaser of the present invention at least has the following advantages:

(1) with sample storage function: after the nucleic acid of the sample is released, it can protect the nucleic acid from degradation for a long time, and the nucleic acid can be stored for 72 hours without degradation under normal temperature conditions;

(2) no pre-processing is required, and the sample is inactivated and lysed directly at room temperature to achieve the release of nucleic acid;

(3) it can be directly used for PCR amplification, without pre-processing, and does not affect the subsequent PCR effect;

(4) the operation is extremely simple, does not rely on any external equipment, has no pollution, and has very low nucleic acid loss: after collecting the sample, only need to turn it upside down for 5-10 times or shake for 30 seconds, and for clinical sample inactivation, lysis and release of nucleic acid are all performed in the same tube;

(5) short time-consuming: after the sample collection is completed, it only takes 15 minutes to complete the release of the nucleic acid of the sample, and the nucleic acid solution can be obtained after an instantaneous centrifugation; and (6) the risk of contamination to laboratories and experiment operators is small: the entire process of releasing the nucleic acid is carried out at room temperature, which can effectively reduce the pollution of aerosols and effectively protect the experiment operators.

Therefore, compared with traditional nucleic acid detection, the present invention is a good supplement and alternative. In the event of sudden infectious diseases, the sample releaser of the present invention has obvious advantages in sample collection-storage-transport-inactivation-nucleic acid extraction, such as fast, safe, stable, efficient, and low cost.

Note: the term "inactivation" mentioned herein refers to that: the polar organic solvent and surfactant contained in the releaser can theoretically rupture cells and denature proteins to a certain extent, so that the virus inactivates and has no infectious ability.

DETAILED DESCRIPTION

Figure 1:
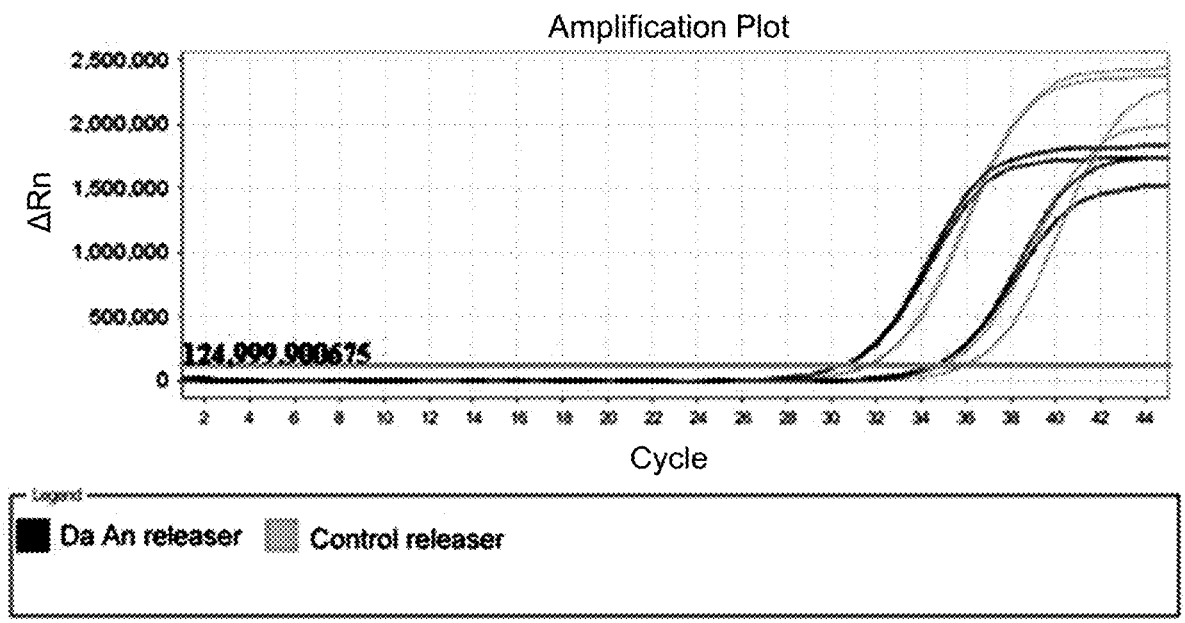
FIG. 1 is a fluorescence quantitative PCR amplification diagram of a sample releaser of the present invention and a commercially available releaser of a certain company to extract clinical samples 1 and 2 of 2019-nCoV.

The present invention is further described below in combination with the accompanying drawings and specific embodiments, but the embodiments do not limit the present invention in any form. Unless otherwise specified, reagents, methods and equipment used in the present invention are conventional reagents, methods and equipment in the art.

Unless otherwise specified, reagents and materials used in the following embodiments are all commercially available.

Embodiment 1

A swab sample nucleic acid releaser includes the following components:

(1) metal ion chelating agent: 5 mol/L of EDTA;
(2) buffer: 50 mmol/L of Tris-buffer at pH 8.5;
(3) polar organic solvent: 25% of DMSO;
(4) surfactant: 2% of Triton X-100; and
(5) nuclease inhibitor: 0.3 mol/L of guanidine hydrochloride.

2. A use method of the above sample releaser was as follows: a nasopharyngeal swab was put into a sample collection tube containing the sample releaser, the sample collection tube was turned upside down and mix well manually for 30 seconds at room temperature, and let stand for 5 minutes, and turned upside down again for 30 seconds, after an instantaneous centrifugation, nucleic acid of the sample was released into the sample releaser, and a supernatant was the released nucleic acid solution.

The obtained nucleic acid solution can be directly pipetted and added to a PCR reaction solution, and then amplified on a PCR amplification machine.

Embodiment 2

A swab sample nucleic acid releaser includes the following components:
(1) metal ion chelating agent: 10 mol/L of EGTA;
(2) buffer: 60 mmol/L of sodium citrate buffer at pH 8;
(3) polar organic solvent: 30% of DMSO;
(4) surfactant: 5% of NP-40; and
(5) nuclease inhibitor: 0.5 mol/L of guanidine isothiocyanate.

Embodiment 3

A swab sample nucleic acid releaser includes the following components:
(1) metal ion chelating agent: 1 mol/L of citric acid;
(2) buffer: 40 mmol/L of sodium phosphate buffer at pH 9;
(3) polar organic solvent: 40% of hexamethylphosphoramide;
(4) surfactant: 1% of SDS; and
(5) nuclease inhibitor: 1 mol/L of 4,4'-carbonylbis(2-(1-naphthoylamino)benzoic acid).

Embodiment 4

A swab sample nucleic acid releaser includes the following components:
(1) metal ion chelating agent: 20 mol/L of EDTA;
(2) buffer: 80 mmol/L of sodium acetate buffer at pH 6;
(3) polar organic solvent: 5% of N,N,N',N'-Tetramethyl-ethylenediamine; (4) surfactant: 10% of Tween-20; and
(5) nuclease inhibitor: 1 mol/L of guanidine hydrochloride.

Embodiment 5

A swab sample nucleic acid releaser includes the following components:
(1) metal ion chelating agent: 1 mol/L of EDTA;
(2) buffer: 5 mmol/L of Tris-buffer at pH 9;
(3) polar organic solvent: 40% of DMSO;
(4) surfactant: 2% of SDS and 2% of Tween-20; and
(5) nuclease inhibitor: 0.1 mol/L of guanidine hydrochloride.

Embodiment 6

1. Experimental Materials
(1) the swab sample nucleic acid releasers of Embodiments 1-5;
(2) a releaser purchased from a certain company: its main components included: 0.1 mmol/L of lithium dodecyl sulfate (surfactant), 50 mmol/L of KCl, 0.1% (W/V) of SDS, and 1% (V/V) of ethanol.
2. The swab sample nucleic acid releasers of Embodiments 1-5 were used to extract the clinical positive samples 1 and 2 of 2019-nCoV (provided by Yunkang Clinical Laboratory Center) collected in Guangzhou from January to March 2020, respectively. The obtained nucleic acid solution was used as a template, and it was directly pipetted into the PCR reaction solution, and then amplified on the PCR amplification machine.

At the same time, a commercially available releaser from a certain company was used as a control. Clinical positive samples of swabs were taken and sampled in parallel at the same time to extract nucleic acid according to the manufacturer's instructions, and the extracted nucleic acid was taken for PCR detection.

In particular, the PCR amplification kit used for the nucleic acid PCR detection was the new coronavirus 2019-nCoV nucleic acid detection kit (fluorescence PCR method) of Da An Gene Co., Ltd. of Sun Yat-sen University (National Medical Devices Registration No. 20203400063).

The PCR system is shown in Table 1:

TABLE 1

| Amplification system | Template amount | Total volume |
|---|---|---|
| 20 | 5 | 25 |

The specific PCR amplification procedures are shown in Table 2:

TABLE 2

| Step | Cycle number | Temperature | Time |
|---|---|---|---|
| 1 | 1 | 50° C. | 15 minutes |
| 2 | 1 | 95° C. | 15 minutes |
| 3 | 45 | 94° C. | 15 seconds |
|   |   | 55° C. | 45 seconds |

Figure 2:
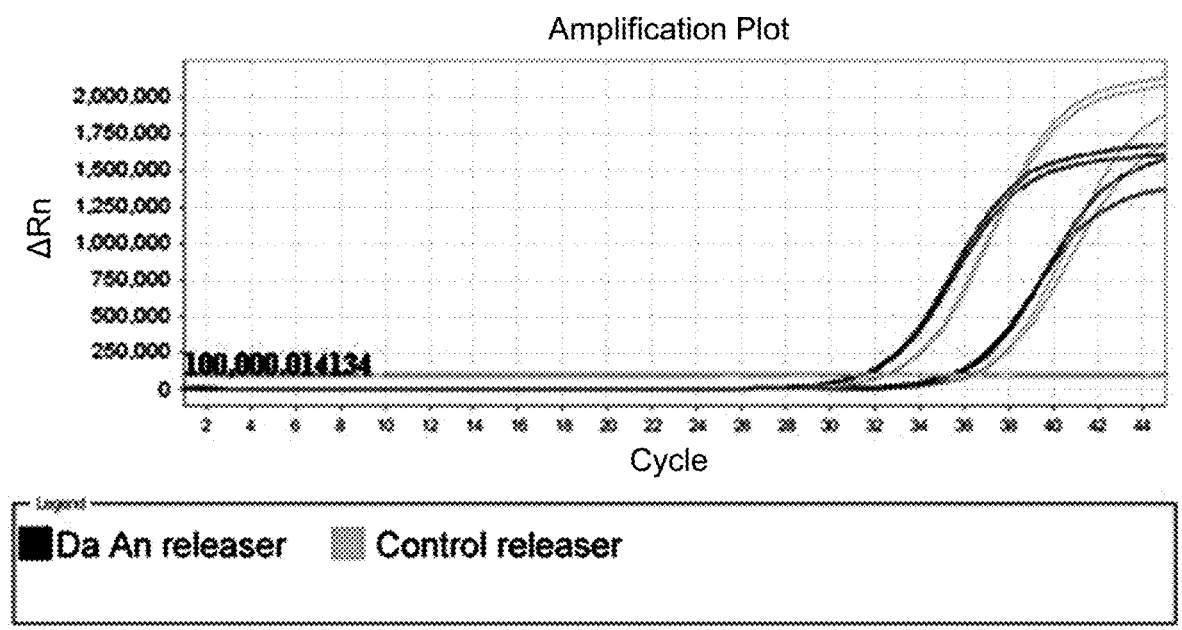
FIG. 2 is a fluorescence quantitative PCR amplification diagram of a sample releaser of the present invention and a commercially available releaser of a certain company to extract clinical samples 1 and 2 of 2019-nCoV.

2. The amplification results are shown in Table 3 and FIGS. 1-2, and the amplification results of Embodiment 1 is taken as an example.

The results show that the Ct value of clinical samples of 2019-nCoV extracted by the sample releaser of the present invention is about 1-3 Ct less than that of the same sample extracted by the sample releaser of a certain company in the market, and the extraction effect of the present invention sample releaser is significantly better than that of the control releaser.

TABLE 3

| Ct value of fluorescence quantitative PCR amplification | Target | Clinical sample 1 | | Clinical sample 2 | |
|---|---|---|---|---|---|
| Sample releaser of Embodiment 1 | N | 30.2 | 30.1 | 34.3 | 34.1 |
|  | 1ab | 31.3 | 31.4 | 35.7 | 35.3 |
| Sample releaser of Embodiment 2 | N | 30.2 | 30.0 | 34.2 | 34.2 |
|  | 1ab | 31.4 | 31.1 | 35.3 | 35.2 |
| Sample releaser of Embodiment 3 | N | 30.0 | 30.1 | 34.2 | 34.0 |
|  | 1ab | 31.1 | 31.1 | 35.1 | 35.2 |
| Sample releaser of Embodiment 4 | N | 29.9 | 29.2 | 33.9 | 33.7 |
|  | 1ab | 30.2 | 30.2 | 34.2 | 34.2 |
| Sample releaser of Embodiment 5 | N | 29.2 | 29.7 | 32.2 | 32.1 |
|  | 1ab | 33.0 | 30.0 | 33.1 | 33.2 |
| Commercially available sample releaser of a certain company | N | 31.8 | 31.7 | 36.1 | 35.0 |
|  | 1ab | 32.6 | 32.7 | 36.3 | 36.5 |

Embodiment 7

Releaser Stability Test (Storage Effect on Samples):

Clinical samples: clinical positive samples 3 and 4 of 2019-nCoV collected in Guangzhou from January to March 2020 (provided by Yunkang Clinical Laboratory Center)

Embodiment 1 was taken as an example, the sample releaser of the present invention was used to store clinical samples 3 and 4 of 2019-nCoV at room temperature for 3 days, 4° C. for 7 days, and −20° C. for 15 days, respectively, and then fluorescent quantitative PCR amplification was performed. The PCR amplification kit used for PCR detection was the 2019-nCoV nucleic acid detection kit (fluorescence PCR method) (National Medical Devices Registration No. 20203400063) of Da An Gene Co., Ltd. of Sun Yat-sen University.

The Ct value data is shown in Table 4 to Table 6. The stable storage of nucleic acid shows that whether it is low temperature −20° C., 4° C., or room temperature, the sample releaser has a very good storage effect on nucleic acid samples.

TABLE 4

After placing for a period of time (3 days at room temperature):

| Time (day) | Sample 3 Target | | Time (day) | Sample 4 Target | |
|---|---|---|---|---|---|
| | N | 1AB | | N | 1AB |
| 0 | 26.4 | 29.3 | 0 | 29.8 | 33.0 |
| 1 | 26.5 | 29.5 | 1 | 29.9 | 33.1 |
| 2 | 26.6 | 29.7 | 2 | 30.1 | 33.3 |
| 3 | 26.6 | 29.8 | 3 | 30.1 | 33.6 |
| Average | 26.5 | 29.6 | Average | 30.0 | 33.2 |
| Stdev | 0.092 | 0.218 | Stdev | 0.155 | 0.267 |
| CV % | 0.345% | 0.735% | CV % | 0.516% | 0.805% |

TABLE 5

After placing for a period of time (7 days at 4° C.):

| Time (day) | Sample 3 Target | | Time (day) | Sample 4 Target | |
|---|---|---|---|---|---|
| | N | 1AB | | N | 1AB |
| 0 | 26.4 | 29.3 | 0 | 29.8 | 33.0 |
| 3 | 26.6 | 29.8 | 3 | 29.9 | 33.7 |
| 5 | 26.5 | 30.3 | 5 | 30.0 | 34.1 |
| 7 | 26.4 | 30.3 | 7 | 29.8 | 33.7 |
| Average | 26.5 | 29.9 | Average | 29.9 | 33.6 |
| Stdev | 0.075 | 0.461 | Stdev | 0.107 | 0.467 |
| CV % | 0.283% | 1.542% | CV % | 0.358% | 1.388% |

TABLE 6

After placing for a period of time (15 days at −20° C.):

| Time (day) | Sample 3 Target | | Time (day) | Sample 4 Target | |
|---|---|---|---|---|---|
| | N | 1AB | | N | 1AB |
| 0 | 26.4 | 29.3 | 0 | 29.8 | 33.0 |
| 3 | 26.7 | 29.9 | 3 | 29.9 | 33.4 |
| 7 | 26.3 | 30.2 | 7 | 29.8 | 33.7 |
| 10 | 26.4 | 30.4 | 10 | 29.8 | 33.8 |
| 12 | 26.6 | 30.7 | 12 | 30.0 | 34.2 |
| 15 | 26.3 | 30.4 | 15 | 30.0 | 34.4 |
| Average | 26.5 | 30.2 | Average | 29.9 | 33.8 |
| Stdev | 0.167 | 0.471 | Stdev | 0.107 | 0.535 |
| CV % | 0.633% | 1.563% | CV % | 0.359% | 1.586% |

Embodiment 8

1. Clinical Sample

Clinical positive sample 3 of 2019-nCoV collected in Guangzhou from January to March 2020 (provided by Yunkang Clinical Laboratory Center)

2. Experimental Material (1) Experimental group: the sample releaser of Embodiment 1

(2) Control group 1, the sample releaser has following compositions:
buffer: 50 mmol/L Tris-buffer at pH 8.5;
polar organic solvent: 25% DMSO;
surfactant: 2% Triton X-100; and
nuclease inhibitor: 0.3 mol/L guanidine hydrochloride.

(3) Control group 2, the sample releaser has following compositions:
metal ion chelating agent: 5 mol/L EDTA;
buffer: 50 mmol/L Tris-buffer at pH 8.5; and
nuclease inhibitor: 0.3 mol/L guanidine hydrochloride.

(4) Control group 3, the sample releaser has following compositions:
metal ion chelating agent: 5 mol/L EDTA;
buffer: 50 mmol/L Tris-buffer at pH 8.5;
surfactant: 2% Triton X-100; and
nuclease inhibitor: 0.3 mol/L guanidine hydrochloride.

(5) Control group 4, the sample releaser has following compositions:
buffer: 50 mmol/L Tris-buffer at pH 8.5;
surfactant: 2% Triton X-100; and
nuclease inhibitor: 0.3 mol/L guanidine hydrochloride.

(6) Control group 5, the sample releaser has following compositions:
metal ion chelating agent: 5 mol/L EDTA;
polar organic solvent: 25% DMSO;
surfactant: 2% Triton X-100; and
nuclease inhibitor: 0.3 mol/L guanidine hydrochloride.

(7) Control group 6, the sample releaser has following compositions:
metal ion chelating agent: 5 mol/L EDTA;
buffer: 50 mmol/L Tris-buffer at pH 8.5;
polar organic solvent: 25% DMSO; and
nuclease inhibitor: 0.3 mol/L guanidine hydrochloride.

3. Experimental Method

Embodiment 1 was taken as an example, the sample releaser of the present invention was used to treat clinical sample 3 of 2019-nCoV, and then fluorescent quantitative PCR amplification was performed. The PCR amplification kit used for PCR detection was the 2019-nCoV nucleic acid detection kit (fluorescence PCR method) (National Medical Devices Registration No. 20203400063) of Da An Gene Co., Ltd. of Sun Yat-sen University.

4. The amplification results are shown in Table 7. The results show that the Ct value of the 2019-nCoV clinical samples extracted by the sample releaser of the present invention is about 3-6 Ct higher than that of the same sample extracted by the control groups. The extraction effect of the sample releaser of the present invention is significantly better than the control releasers.

TABLE 7

| Ct value of fluorescence quantitative PCR amplification (target N gene) | |
|---|---|
| Experimental group | 26.0 |
| Control group 1 | 29.0 |
| Control group 2 | 30.3 |
| Control group 3 | 30.8 |
| Control group 4 | 30.5 |
| Control group 5 | 28.7 |
| Control group 6 | 27.9 |

5. In addition, the above-mentioned nucleic acid samples extracted with the releasers of the experimental group and the control groups 1-6 were placed at room temperature for 3 days and then subjected to fluorescence quantitative PCR amplification. The Ct value data is shown in Table 8.

TABLE 8

Ct value of the target N gene after the nucleic acid sample is placed at room temperature for 3 days

| Releaser group | Time (day) | | | |
|---|---|---|---|---|
| | 0 | 1 | 2 | 3 |
| Embodiment 1 | 25.9 | 26.1 | 26.3 | 26.4 |
| Control group 1 | 28.2 | 29.3 | 31.4 | 33.6 |
| Control group 2 | 31.5 | 32.8 | 35.4 | 37.9 |
| Control group 3 | 29.6 | 30.5 | 32.1 | 35.7 |
| Control group 4 | 30.1 | 32.2 | 33.7 | 36.5 |
| Control group 5 | 29.2 | 31.5 | 33.4 | 37.8 |
| Control group 6 | 28.7 | 30.1 | 32.7 | 36.9 |

The above-described embodiments are preferred implementations of the present invention, but the implementations of the present invention are not limited by the above-described embodiments. Any other changes, modifications, substitutions, combinations, and simplifications made without departing from the spirit and principle of the present invention shall be equivalent replacements and shall be included in the scope of protection of the present invention.

What is claimed is:

1. A swab sample nucleic acid releaser, comprising the following components:
    (1) 1 mol/L of a metal ion chelating agent;
    (2) 40 mmol/L of a buffer at pH 9;
    (3) 40% (v/v) of a polar organic solvent;
    (4) 1% (v/v) of a surfactant; and
    (5) 1 mol/L of a nuclease inhibitor, wherein the metal ion chelating agent is citric acid; the buffer is a sodium phosphate buffer; the polar organic solvent is hexamethylphosphoramide; the surfactant is SDS; and the nuclease inhibitor is 4,4'-carbonylbis(2-(1-naphthoylamino)benzoic acid).

2. A method of swab sample storing and nucleic acid releasing, comprising: putting a swab into a container containing the sample releaser according to claim 1, turning the container upside down and mixing for 20- 40 seconds at room temperature, letting stand for 10-20 minutes, and turning upside down again for 20-40 seconds, after an instantaneous centrifugation, a supernatant in the container comprises released nucleic acid.

3. A swab sample nucleic acid releasing kit, wherein the kit contains the sample releaser according to claim 1.

* * * * *